(12) United States Patent
Amar et al.

(10) Patent No.: US 7,892,483 B2
(45) Date of Patent: Feb. 22, 2011

(54) STERILIZATION PROCESS

(75) Inventors: Lulla Amar, Maharashtra (IN); Geena Malhotra, Maharashtra (IN)

(73) Assignee: CIPLA Limited, Mumbai (IN)

( * ) Notice: Subject to any disclaimer, the term of this patent is extended or adjusted under 35 U.S.C. 154(b) by 512 days.

(21) Appl. No.: 11/077,363

(22) Filed: Mar. 11, 2005

(65) Prior Publication Data

US 2005/0201888 A1 Sep. 15, 2005

(30) Foreign Application Priority Data

Mar. 12, 2004 (IN) .................. 313/MUM/2004

(51) Int. Cl.
- *A61L 2/00* (2006.01)
- *A61L 2/04* (2006.01)
- *A61L 9/00* (2006.01)
- *A61L 11/00* (2006.01)
- *C23F 11/00* (2006.01)

(52) U.S. Cl. .......................................... 422/1

(58) Field of Classification Search ................. 514/169; 422/1

See application file for complete search history.

(56) References Cited

U.S. PATENT DOCUMENTS

| | | | | |
|---|---|---|---|---|
| 3,962,430 A | * | 6/1976 | O'Neill | 514/64 |
| 4,347,238 A | * | 8/1982 | Hollingsbee | 514/157 |
| 4,939,135 A | * | 7/1990 | Robertson et al. | 514/179 |
| 6,071,904 A | * | 6/2000 | Ali et al. | 514/222.8 |
| 6,241,969 B1 | * | 6/2001 | Saidi et al. | 424/45 |
| 6,245,349 B1 | * | 6/2001 | Yiv et al. | 424/450 |
| 6,392,036 B1 | | 5/2002 | Karlsson et al. | |
| 6,464,958 B1 | * | 10/2002 | Bernini et al. | 424/43 |
| 6,863,865 B2 | * | 3/2005 | McAffer et al. | 422/38 |
| 7,084,153 B2 | * | 8/2006 | Banholzer et al. | 514/291 |
| 2001/0051131 A1 | * | 12/2001 | Unger | 424/9.5 |
| 2003/0103864 A1 | * | 6/2003 | McAffer et al. | 422/1 |
| 2003/0119802 A1 | | 6/2003 | Gavin | |
| 2003/0129242 A1 | * | 7/2003 | Bosch et al. | 424/489 |

FOREIGN PATENT DOCUMENTS

| | | |
|---|---|---|
| EP | 0 693 292 A | 1/1996 |
| WO | WO 01/78744 A | 10/2001 |
| WO | WO 01/78745 A | 10/2001 |
| WO | WO 02/39993 A | 5/2002 |
| WO | WO 02/089815 A | 11/2002 |
| WO | WO 03/086348 A | 10/2003 |

\* cited by examiner

*Primary Examiner*—Elizabeth McKane
*Assistant Examiner*—Regina Yoo
(74) *Attorney, Agent, or Firm*—Nixon & Vanderhye

(57) ABSTRACT

Process for the sterilization of a steroid, in which the steroid is heat treated in the form of a wet mass comprising the steroid, water and an excipient.

22 Claims, 1 Drawing Sheet

STERILIZATION PROCESS

The present invention relates to a process for the sterilization of steroids, particularly glucocorticosteroids and to the use of steroids so sterilized in sterile pharmaceutical formulations.

BACKGROUND OF THE INVENTION

Sterilization is a process performed to ensure that there is complete freedom from microbial contamination. Sterilization is especially done for pharmaceutical formulations which are to be directly introduced into the body and its cavities. Such formulations explicitly include ophthalmic preparations, nasal preparations, ocular preparations, injectables, transdermal patches, depot preparations and the like. Such sterilized preparations involve two main methods of preparation. First route is that the active ingredient is sterilized and the formulation is prepared aseptically or the final is prepared, packed in the desired container and then sterilized. The second route is known as a terminal sterilization technique.

Certain formulations such as respules or aqueous nasal preparations, ophthalmic preparations and the like that involve steroids as the active ingredient are usually prepared by the first method described above. The most important reason being that these formulations are usually packed in containers made from LDPE which are not suitable for terminal sterilization.

Several patents disclose the methods of sterilization of active ingredients. PT-A-69652 discloses the cold sterilization of micronized glucocorticosteroids using mixtures of ethylene oxide and carbon dioxide, since according to PT-A-69652, steroids in powder form are not stable at temperatures above 60° C. Specific examples of glucocorticosteroids are prednacindone, budesonide, dexamethasone and prednisolone, and salts, esters and fluro derivatives thereof, including dexamethasone acetate, dexamethasone phosphate, prednisolone pivalate and 9-alphafluoro prednisolone.

However, ethylene oxide is toxic and when it is used to sterilize glucocorticosteroids it has been found that the residual amounts of the ethylene oxide contravene pharmaceutical guidelines, which require very low levels of residual ethylene oxide. Accordingly this method has been found to be unsuitable for producing therapeutically acceptable glucocorticosteroids and formulations thereof.

U.S. Pat. No. 3,962,430 discloses a method for the production of sterile isotonic solutions of medicinal agents, which comprises adding the agent to a saturated solution of sodium chloride in water at 100° C. and then heating the mixture at 100-130° C. This method is not suitable for suspensions of fine particles of steroids, which are intended for inhalation because the water, and the heating and cooling involved, produce unfavourable changes in the size of particles. Indeed it can lead to the formation of bridges between the fine particles producing large, hard aggregates, which will not deaggregate into the desired fine particles upon administration.

A putative alternative is dry heat sterilization. According to the European Pharmacopoeia (1996, pp. 283-4) a normal heat sterilization process runs at 180° C. for 30 min or at a minimum of 160° C. for at least 2 hours. According to Pharmacopeia Nordica (1964, pp. 16) such sterilization can be carried out at 140° C. for 3 hours. However at the temperatures of these processes glucocorticosteroids suffer significant degradation and are subject to changes in their surface structure.

Sterilization by $\beta$ or $\gamma$-irradiation is also known. Indeed Illum and Moeller in Arch. Pharm. Chemi. Sci., Ed. 2, 1974, pp. 167-174 recommend the use of irradiation to sterilize glucocorticosteroids. However when such irradiation is used to sterilize certain finely divided, e.g., micronized steroids such as glucocorticosteroids, they are significantly degraded.

WO-A-96/09814 to Andaris Ltd. relates to spray-dried particles of a water-soluble material with a mass median particle size of 1 to 10 μm. The aim of the invention is to produce forms and respirable particles for use in dry powder inhalers. The water-soluble material is preferably a human protein or a fragment thereof, in natural or recombinant form, e.g., human serum (HAS), alpha-1 antitrypsin or alcohol dehydrogenase. Also combinations of an active material with a carrier were produced e.g., budesonide and lactose. It is stated generally that the microparticles produced can be sterile without teaching how this could or would be neither achieved or showing any proof thereof.

WO-A-96/32095 to Astra AB relates to a process for the preparation of respirable particles by dissolving an inhalation compound in a solvent, introducing the resulting solution containing the inhalation compound in droplet form or as a jet stream into an anti-solvent which is miscible with the solvent and which is under agitation. Budesonide with a mass median diameter (MMD) of less than 10 μm is produced with the process. There is no information n WO-A-96/32095 about sterilization or sterile particles.

A method for sterilizing biological materials by irradiation over a temperature gradient is discussed in U.S. patent application No. 20040033160 by MacPhee et al. US patent Publication No. 20040022673 by Protic. deals with a sterilization process and apparatus therefore. U.S. patent Publication 20040001774 by Williams et al. (Johnson & Johnson) discloses sterilization with temperature-controlled diffusion path. A chemical vapour sterilization process and system with heat pump operated vaporizer/condenser is discussed in US patent Publication No. 20040033161 by Kendall et al. (Johnson & Johnson). High pressure sterilizing of sensitive active principles, particularly peptides, oligonucleotides and proteins are disclosed in US patent Publication No. 2003103863 by Grislain et al. Attempts at terminal sterilization of pharmaceutical formulations, especially suspensions, e.g., aqueous suspensions, of glucocorticosteroids have all proved unsatisfactory. Such suspensions can not normally be sterilized by sterile filtration as most of the particles of glucocorticosteroids will be retained on the filter. Moist heat sterilization, e.g., steam treatment of glass vials containing the product, leads to an unacceptable change in particle size.

Various aqueous suspensions of finely divided glucocorticosteroids are known e.g., the budesonide-containing product known as Pulmicort® nebulising suspension. (Pulmicort® is a trademark of Astra AB of Sweden). Similar formulations of fluticasone propionate are known from WO-A-95/31964.

WO 99/25359 discloses a process for the sterilization of a glucocorticosteroid which process comprises heat-treating the glucocorticosteroid in the form of a powder at a temperature of from 100 to 130° C. However, we have found that by this method final formulations show a considerable rise in impurity levels.

SUMMARY OF THE INVENTION

We have now found that, surprisingly, steroids, particularly glucocorticosteroids such as budesonide, can in fact be satisfactorily sterilized without resorting to irradiation or dry sterilization techniques or to the use of saturated solutions of sodium chloride.

According to the present invention there is provided a process for the sterilization of a steroid which process comprises heat treating the steroid in the form of a wet mass comprising steroid, water and an excipient.

The present process produces a much lower level of total impurities, in particular degradation products of the steroid, than the prior art sterilizations.

The invention seeks to provide a sterilized wet mass which comprises active ingredient selected from steroids and such other drugs of this class without degradation of the active ingredient.

The present invention also aims at providing the use of this sterile wet mass, which can be used in preparations, or formulations, which are required to be sterile but cannot be terminally sterilized.

The present invention relates of a method of active pharmaceutical molecules, that are susceptible to high temperatures. The method involves forming a wet mass of the active ingredient preferably along with one or more pharmaceutically suitable excipients and one or more vehicles therefor. The sterilized mass containing the sterilized active ingredient thereof can be used in the preparation of formulations that are required to be sterile.

The steroids which may be used in the present invention include but are not limited to betamethasone, fluticasone (e.g., as propionate), budesonide, tipredane, dexamethasone, beclomethasone (e.g., as diproprionate), prednisolone, flucinolone, triamcinolone (e.g., as acetonide), mometasone (e.g., as furoate), rofleponide (e.g., as palmitate), flumethasone, flunisolide, ciclesonide, deflazacort, cortivazol, 16a,17a-butylidenedioxy-6a,9a-difluro-11 ss, 21-dihydroxy-pregna-1, 4-diene3,20-dione; 6a,9a-difluro-11 ss-hydroxy-16a,17a-butylidenedioxy-17ss-methylthio-androsta-4-ene-3-one; 16a, 17a-butylidenedioxy-6a,9a-difluoro-11 ss-dydroxy-3-oxo-androsta-1,4-diene-17p-carbothioic acide S-methyl ester; methyl19a-chloro-6a-fluoro-11 ss-hydroxy-16oc-methyl-3-oxo-17a-propionyloxy-androsta-1,4-diene-17a-carboxylate; 6a,9a-difluoro-11 ss-hydroxy-16a-methyl-3-oxo-17a-propionyloxy-androsta-1,4-diene-17p-carbothioic acid-(2-oxo-tetrahydrofuran-3-yl) ester; optionally in their pure isomeric forms (where such forms exist) and/or in the form of their esters, acetals or salts, where applicable. For use in preparations where the drug must reach the small cavities, such at the bronchi, the cornea and such other minute cavities, the active pharmaceutical ingredient is preferably in finely divided particulate form. For example, it may be micronised before sterilization. The mass median diameter (MMD) of the particles is preferably less than about 10 μm.

The steroid is preferably in finely divided particulate form, with 90% of the particles preferably having a diameter of less than 10 μm. More preferably, 90% of the particles have a diameter of less than 5 μm. The present sterilization method does not significantly affect the particle size and this is an advantageous feature. Generally speaking, after sterilization according to the present invention, the particle size is substantially the same as it was before sterilization.

Particularly preferred steroids include budesonide, fluticasone (especially as the propionate), triaminolone (especially as the acetonide), prednisolone, and mometasone (especially as the furoate).

We have found water which is relatively free, preferably substantially free of ionic species to be particularly satisfactory. We prefer to use purified water, distilled water or water for injection (WFI). These terms are well understood in the art, and reference can be made to US Pharmacopoeia (USP) 23 Monograph for further definitions.

The invention is, in part, based upon using as little water as necessary in the wet mass. The exact quantity may vary and will depend upon the steroid used, but in principle the amount of water will be less than that required for the steroid to go into solution, or at least to dissolve and recrystallise in any significant amount. The wet mass, is, therefore, preferably a moist slurry. During sterilization preferably most of the water in the wet mass turns to steam, thus effectively "steam treating" the steroid so as to render it sterile. Suitably, therefore, the wet mass comprises a sufficient amount of water so as to give enough steam for sterilization of the steroid.

Preferably, the amount of water is about or less than ten times, more preferably about or less than five times, the amount of steroid by weight. The ratio may be one part steroid to two or three parts water (by weight) or less, depending on the active. About one part steroid to above two parts water (by weight) is suitable for some actives, particularly budesonide. By "about", we mean up to plus or minus 10%, unless otherwise indicated. Ratios of from about 1:1 to about 1:10 (active: water) by weight may be used.

It is highly preferred to use a wet mass comprising steroid, water and one or more surfactants. Any suitable surfactant may be used, but we prefer to use surfactants such as polyoxyethylene esters of sorbitol anhydrides (Tweens), the same compounds without the hydrophilic oxyethylene groups (Spans), higher molecular weight polyethylene glycols, and molecular combinations of polyoxyethylene and polyoxypropylenes. Polysorbates, for example polysorbate 80, and sorbitan fatty acid esters are among the preferred compounds.

The amount of surfactant may vary, but is preferably sufficient to ensure adequate wetting of the steroid particles with the water. Suitably, the surfactant may be used in an amount of from 0.0001% to 0.5% by weight of the mass.

A viscosity modifying agent may be included in the wet mass if desired, and any suitable agent for modifying the viscosity of aqueous pharmaceutical formulations may be used, as will be clear to those skilled in the art of formulation. We prefer, however, to use a wet mass comprising only steroid, water and surfactant. Budesonide, water and polysorbate 80 is an example of a preferred composition, preferably with a ratio (by weight) of budesonide to water of from about 1:1 to about 1:7. Ratios of about 1:2 and 1:5 have been found to give good results.

The present invention relates to a method of sterilizing active pharmaceutical ingredients, such as steroids that are susceptible to higher temperatures. The method involves introducing the active ingredient into a pressure vessel or other sealed container along with one or more excipients (preferably surfactant) and water. The pressure vessel is preferably fitted with a hydrophobic vent filter and a hydrophobic cartridge filter. The sterilization is preferably done at temperatures ranging from 100-140° C. for 3-30 mins at varying pressures.

Preferred combinations of temperature-time-pressure including the following:

(a) 121° C. for 20 mins at 15 psi.

(b) 132° C. for 3 mins at 27 psi.

(c) 115° C. for 30 mins at 10 psi.

but other combinations can be used if desired. Generally, the higher the temperature and pressure, the shorter the time required for adequate sterilization.

In the present invention, a wet mass preferably comprising steroid, excipient (preferably surfactant) and water is, for example, placed in a pressure vessel or other sealed container. This vessel or container is then preferably placed in an autoclave, and then sterilization takes place. This differs from other methods in which material containing the active ingredient of interest is placed in an autoclave and sterilized directly. The present methods confers the advantage of being able to transfer the sterilized mass directly to the main bulk of the final formulation (for example, a nasal spray or respule formulation) without intermediate steps, in particular without using sterilization chambers.

Thus, in another aspect, the invention provides a process for making an aqueous pharmaceutical formulation containing a sterile steroid, which process comprises placing a wet mass comprising the steroid, water and an excipient in a pressure vessel or other sealed container, heat treating the wet mass to sterilize the steroid, and directly transferring the sterilized mass to the remaining bulk of the formulation. Preferably, surfactant is also included in the wet mass.

Preferably, the transfer is done aseptically. Also, the remaining bulk of the formulation is preferably sterile. In this way, a sterile aqueous formulation can be produced.

For example, after sterilization, tubing can be attached to the pressure vessel or other container used for the sterilization, to connect it directly to a container containing the main bulk of the formulation. Using nitrogen purging the sterilized wet mass may be transferred directly from the pressure vessel to the other container where it may be mixed to give a final formulation.

Preferably, at the end of sterilization the sterilized mass still contains a small quantity of water—that is to say, it is not completely dry. Suitably, the sterilized mass comprises at least 1% (by total weight of the mass) water, preferably at least 5% by weight, but more or less water can be present if desired, depending on the active.

Generally speaking, simple mixing of the ingredients will be sufficient to form the initial wet mass, as will be understood.

Preferably the vessel used for sterilization is a conventional vessel fitted with attachments such as a vent filter, cartridge filter and the like. The sterilization of the wet mass results in preparations (for example, nasal sprays or respules) with reduced impurities as compared to preparations in which the API was sterilized by other methods such as dry heat sterilization, gamma-radiation sterilization and simply moist heat sterilization. This is because these molecules are highly susceptible to temperatures above 60° C., and sterilization is usually done at temperatures above 100° C. A comparative impurity profile for budesonide is shown below. It illustrates the various impurities resulting from different methods of sterilization as compared to the method of the invention. The figures refer to % by weight of budesonide.

Figure 1:
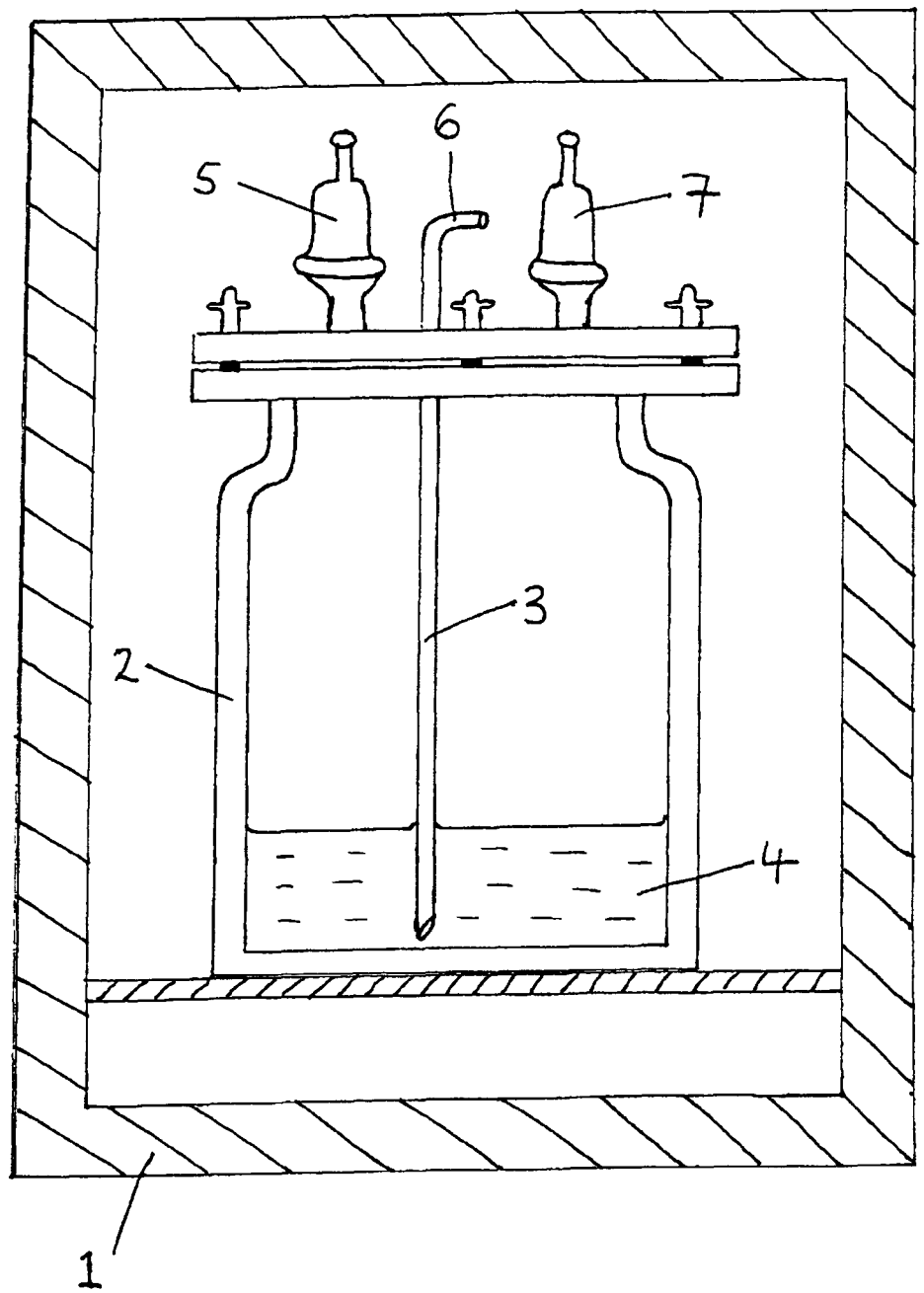
FIG. 1 illustrates an autoclave (1) containing a 5 liter SS 316L pressure vessel (2) containing a wet mass (4) comprising batch quantities of drug, water for injection and polysorbate 80. The ratio (by weight) of drug to water is 1:2.

The wet mass (4) after being sterilized may be transferred to the bulk solution (not shown in the figure) through the product outlet (6), which is connected to a vessel containing bulk solution. The pressure vessel (2) is also provided with air filter housing (7) for release of steam. The pressure vessel (2) is further provided with a product filter with housing (5), which may be necessary in order to transfer some bulk solution to the base solution in order to remove the remaining quantity of base solution when the pressure in the pressure vessel (2) is low. Both housing (5) and housing (7) are provided with 0.22 micron filters in order to maintain sterility of the base solution.

The wet mass can be used in the preparation of formulations which are required to be sterile and cannot be sterilized terminally. Such preparations include nasal preparations such as respules or aqueous nasal preparations, ophthalmic preparations and ocular preparations.

The following example illustrates the invention.

EXAMPLE

Example 1

Budesonide Respules 0.5 mg:

| Sr. No. | Ingredients | Quantity (% w/v) |
|---|---|---|
| 1. | Budesonide (micronised) | 0.025 |
| 2. | Disodium edeate | 0.01 |
| 3. | Polysorbate 80 | 0.016 |
| 4. | Sodium chloride | 0.9 |
| 5. | Citric acid monohydrate | q.s. to pH 4 |
| 6. | Water for Injection | 100 ml |

| Impurity | Non-sterile | Gamma-radiation | | | Dry Heat Sterilization | | | Invention |
|---|---|---|---|---|---|---|---|---|
| | | 10 Kgy | 15 Kgy | 25 Kgy | 180° C./ 10 min | 180° C./ 20 mins | 180° C./ 30 min | 121° C./ 30 mins |
| Predisolone | ND | ND | ND | ND | ND | ND | ND | ND |
| D-Homo budesonide | 0.06 | 0.07 | 0.06 | 0.286 | 0.06 | 0.06 | 0.06 | 0.05 |
| Desonide | 0.10 | 0.11 | 0.09 | 0.044 | 0.10 | 0.1 | 0.09 | 0.09 |
| Predisolone-16-Butyrate | 0.02 | 0.15 | 0.21 | 0.062 | 0.05 | 0.07 | 0.07 | 0.04 |
| 21-Dehydro Epimers I and II | ND | 0.10 | 0.12 | 0.284 | 0.07 | 0.09 | 0.10 | ND |
| 1,2-Dehydroepimers I and II | 0.11 | 0.12 | 0.10 | 0.112 | 0.11 | 0.11 | 0.11 | 0.16 |
| Single maximum Unknown impurity | 0.04 | 0.21 | 0.27 | 0.182 | 0.19 | 0.23 | 0.26 | 0.05 |
| Total impurities | 0.37 | 1.21 | 1.42 | 1.298 | 0.9 | 1.03 | 1.12 | 0.5 |

ND = not detectable

Procedure:

Preparation of Base Solution:
1. Take budesonide along with polysorbate 80 and water for injection in the pressure vessel.
2. Sterilize the same by charging in an autoclave at 121 degrees centigrade for 30 minutes.
3. Transfer the sterilized pressure vessel to aseptic area.

Preparation of Bulk Suspension:
1. In water for injection cooled under nitrogen purging, add and dissolve sodium chloride and disodium edentate under stirring.
2. Adjust the pH of suspension to 4.
3. Add the base solution from pre-sterilized pressure vessel to the bulk suspension aseptically.

The invention claimed is:

1. A process for the sterilization of a steroid which process comprises heat treating the steroid in the form of a wet mass consisting essentially of the steroid, water and surfactant, wherein the water is not saturated with respect to any solute present in the water, wherein the amount of water in the wet mass is no more than ten times the amount of steroid and wherein at the end of sterilization the sterilized mass comprises at least 1%, by weight of the total mass, of water.

2. A process according to claim 1 wherein the steroid is budesonide, fluticasone, triamcinolone, prednisolone or mometasone, or a pharmaceutically acceptable derivative thereof.

3. A process according to claim 2 wherein the pharmaceutically acceptable derivative is a salt or ester.

4. A process according to claim 1 wherein the water is purified water, distilled water or water for injection.

5. A process according to claim 1 wherein the steroid is heat treated at a temperature of from 100° C. to 140° C.

6. A process according to claim 1 wherein the heat treatment is done at a pressure of from 5 to 30 psi.

7. A process according to claim 1 wherein the wet mass is heat treated for 3 to 30 minutes.

8. A process according to claim 1 wherein the surfactant is a polyoxyethylene sorbitan fatty acid ester (polysorbate) or a sorbitan fatty acid ester.

9. A process according to claim 1 wherein the sterilization comprises placing the wet mass in a pressure vessel or other sealed container, placing the vessel or container in an autoclave, and heat treating.

10. A process according to claim 1 wherein the steroid is budesonide and the ratio by weight of budesonide to water in the wet mass is about 1:1 to about 1:8.

11. A process according to claim 1 wherein the steroid is in the form of finely divided particles and wherein there is substantially no change in the particle size after sterilization.

12. A process according to claim 1 wherein the steroid is in particulate form with 90% of the particles having a diameter of less than 10 µm.

13. A process according to claim 1 wherein the amount of water by weight in the wet mass is no more than 5 times the amount of steroid by weight.

14. A process according to claim 1 wherein the steroid is heat treated at a temperature of from 115° C. to 135° C.

15. A process according to claim 1 wherein the heat treatment is done at a pressure of from 10 to 20 psi.

16. A process according to claim 1 wherein the steroid is budesonide and the ratio by weight of budesonide to water in the wet mass is about 1:2 to about 1:5.

17. A process according to claim 1 wherein the steroid is in particulate form with 90% of the particles having a diameter of less than 5 µm.

18. A process according to claim 1 wherein the solute includes ions.

19. A process for making an aqueous pharmaceutical formulation containing a sterile steroid, which process comprises placing a wet mass consisting essentially of the steroid, water, and surfactant in a pressure vessel or other sealed container, heat treating the wet mass to sterilize the steroid, and directly transferring the sterilized mass to the remaining bulk of the formulation, wherein at the end of sterilization the sterilized mass comprises at least 1%, by weight of the total mass, of water.

20. A process according to claim 19 wherein the pressure vessel or other sealed container is heat treated in an autoclave.

21. A process according to claim 19 wherein the remaining bulk of the formulation is sterile.

22. A process for the sterilization of a steroid which process comprises:
forming a wet mass consisting essentially of the steroid, water and surfactant, wherein the water is not saturated with respect to any solute, including ions, present in the water, and wherein the amount of water in the wet mass is no more than ten times the amount of steroid; and
heat treating said wet mass to achieve sterilization of the steroid with reduced formation of impurities,
wherein at the end of sterilization the sterilized mass comprises at least 1%, by weight of the total mass, of water.

* * * * *